United States Patent [19]

Lavallee

[11] 4,386,087

[45] May 31, 1983

[54] N-SUBSTITUTED METALLOPORPHYRINS AS ANTI-TUMOR AGENTS AGAINST PS-P-388(P388) LEUKEMIA IN ANIMALS

[75] Inventor: David K. Lavallee, New York, N.Y.

[73] Assignee: Research Foundation of the City University of New York, New York, N.Y.

[21] Appl. No.: 279,422

[22] Filed: Jul. 1, 1981

[51] Int. Cl.$^3$ ............................................. A61K 31/555
[52] U.S. Cl. .................................................... 424/245
[58] Field of Search ........................................ 424/245

[56] References Cited

U.S. PATENT DOCUMENTS 2,858,320 10/1958 Woods et al. ...................... 260/314

FOREIGN PATENT DOCUMENTS 37-4795  1/1962  Japan ..................................... 424/245
42-8629  7/1967  Japan ..................................... 424/245

OTHER PUBLICATIONS

Lavallee et al., Inorganic Chemistry, vol. 13, No. 8, 1974, pp. 2004-2008.

Lavallee, Inorganic Chemistry, vol. 16, No. 4, 1977, pp. 955-957.

Lavallee, Inorganic Chemistry, vol. 15, No. 3, 1976, pp. 691-694.

Ackerman et al., Inorganic Chem., vol. 18, No. 12, 1979, pp. 3358-3364.

*Primary Examiner*—Jerome D. Goldberg
*Attorney, Agent, or Firm*—John S. Roberts, Jr.

[57] ABSTRACT

Alkylating agents have been found to have chemotherapeutic value in cancer treatment. The difficulty of altering the alkylation rate or specificity of alkylating agents is solved by methyl release from metallo N-methyl porphyrins in which the release rate is determined by the particular metal ion of the complex. Moreover, it has been shown that porphyrins accumulate specifically in tumors. Sodium aquo-N-methyltetra (p-sulfophenyl) porphinatocopper (II) trifluoromethanesulfonate has been shown to have activity against lymphocytic PS-P-388 (P388) leukemia in mammals. A wide range of N-substituents and metallo complexes, and their preparation are given. Anti-tumor use is demonstrated against P388 leukemia in animals.

1 Claim, No Drawings

N-SUBSTITUTED METALLOPORPHYRINS AS ANTI-TUMOR AGENTS AGAINST PS-P-388(P388) LEUKEMIA IN ANIMALS

BACKGROUND OF THE INVENTION

Chemotherapeutic value has been found in alkylating agents. In general, it is difficult to alter the alkylation rate or specificity of alkylating agents by rational synthetic schemes. The present invention demonstrates a means to do this by the use of metallo-complexed alkyl substituted porphyrins.

A second consideration in the efficacy of chemotherapeutic agents is the localization of the agent in the tumor. Evidence has been presented to show that some porphyrins accumulate specifically in tumor tissue (M. Tsutsui, et al, *Proc. N.Y. Acad. Sci.*, 244, 674 (1975)).

Tumor localization and alkylating ability present combined in one type of molecule are highly desired and the present invention satisfies these criteria.

PRIOR ART

Japanese Pat. No. 4795/62 to Blood Plasma Corp. of Japan shows that the copper or cobalt complex salt of protoporphyrin has anti-tumor activity.

Japanese Pat. No. 8629/67 to Nippon Blood Bank shows radioactive iron complex of protoporphyrin for diagnosis and cure of malignant tumors.

U.S. Pat. No. 2,858,320 discloses that hematoporphyrin has shown to be useful in fluorescing cancer tissue when subjected to ultraviolet radiation and thus is useful as a diagnostic means.

The following articles discloses synthesis and reaction studies on the N-substituted metalloporphyrins. Review and literature reference are cited therein.

Lavallee, D. K. and Gebala, A. E., "Facile Dissociation of a Copper Porphyrin. Chlorocopper (II) N-methyltetraphenyl porphine." Inorganic Chemistry, Vol. 13, No. 8, (1974) p. 2004.

Lavalee, D. K., "Metal Ion Promoted Demethylation of N-Methyltetraphenylporphinato Copper (II)." Inorganic Chemistry, Vol. 15, No. 3, (1976) p. 691.

Lavallee, D. K., "Metal Ion Promoted Demethylation of N-Methyltetraphenylporphyrin by Nickel (II), Zinc (II), and Manganese (II)." Inorganic Chemistry, Vol. 16, No. 4, (1977) p. 955.

Bain-Ackerman, M. J. and Lavallee, D. K., "Kinetics of Metal-Ion Complexation with N-Methyltetraphenylporphyrin. Evidence concerning a General Mechanism of Porphyrin Metalation." Inorganic Chemistry, Vol. 18, No. 12, (1979) p. 3358.

SUMMARY OF THE INVENTION

Metallo complexes of N-substituted porphyrins serve as anti-tumor chemotherapeutic agents. The particular metal is chosen so that the desired rate of substituent release is achieved.

Alkylating agents usually limited to $C_1$ and $C_2$ hydrocarbons have been shown to have chemotherapeutic value in cancer treatment. The particular metal of a porphyrin complex can control the alkylation release. Moreover, porphyrins have been shown to localize in tumor tissue.

Other organic substituents such as nitrogen and sulfur mustards, epoxides and nitrogen heterocycles may also be attached to the nitrogen atom of the porphyrin. Again the controlled release of these substituents can be governed by careful selection of the metal forming the metallo-porphyrin complex. Thereby a wide range of released substituents is available for anti-tumor activity.

DETAILS OF THE INVENTION

Preparation of N-alkylated porphyrins and metallo complexes.

Preparation of N-Substituted Porphyrins

The following methods may be employed to prepare the N-substituted porphyrin. Suitable mono substituents are methyl and ethyl. The specifics are given in terms of methyl which is preferred.

N-Methyltetraphenylporphine. N-Methyltetraphenyl porphine (N—$CH_3$TPP) was prepared by three methods.

(1) The first method is metathetical to former preparation of N-methylporphyrins. Tetraphenylporphine (TPP) and a 100-fold excess of methyl iodide were sealed in a glass tube and heated on a steam bath for 48 hr. The reaction mixture was then dissolved in chloroform, neutralized with 1 M $NH_4OH$, and extracted twice with $H_2O$. The volume of the reaction mixture was reduced to about 50 ml and chromatographed in 500-mg batches on basic alumina (2 in.×36 in. column) using chloroform as eluent. The column developed three distinct bands. The first was TPP (rose), the second was N-$CH_3$TPP (green on column, elutes as dichroic violet-green), and the last was further methylated products (green). This method yields 5% N-$CH_3$-TPP and 15–20% further methylated products with about 75% of the TPP recovered as unreacted material.

(2) In the second method, TPP in chloroform (e.g., 1.0 g in 500 ml) was refluxed with a 50-fold excess of methyl iodide for several hours. The work-up was the same as in method 1 and yields were comparable.

(3) The best method involved slow addition (4 hr) of a stoichiometric amount of fluoromethylsulfonate (Aldrich Chemical Co. "magic methyl") e.g., 0.523 ml in 500 ml) to a dilute solution of TPP in chloroform (e.g., 4.0 g in 1500 ml). The reaction proceeded at room temperature for 2–3 days. The product was isolated as described above and crystallized from chloroform-ethanol (1:1). The products were N-methyltetraphenylporphine (30% after crystallization), further methylated products (less than 3%), and unreacted TPP (60%). The TPP was recycled to give a total yield of N—$CH_3$TPP of about 80%.

The N—$CH_3$TPP is characterized by its distinctive nmr spectrum, which shows a sharp singlet due to the N-methyl group at 4.11 ppm upfield from TMS ($CDCl_3$). The striking upfield chemical shift is presumably due to interaction with the very aromatic porphyrin ring system. The methyl aromatic ratio is 3:28 as expected. The nmr spectra were recorded using a JEOL 100-MHz instrument.

Visible absorption spectra (Cary 14 spectrophotometer) in DMF adhered to Beer's law throughout the range investigated ($2.24 \times 10^{-3}$ to $3.72 \times 10^{-6}$ M), providing evidence for lack of significant association in this concentration range.

Active hydrogen analysis (Huffman Laboratories, Wheat Ridge, Colo.) gave 0.98 active hydrogen per molecule (percent active hydrogen: calcd, 0.159; found, 0.156). Elemental analysis does not distinguish between TPP (calcd for $C_{44}N_4H_{30}$:C,86.0; N,9.12;H,4.93) and N—$CH_3$TPP (calcd for $C_{45}N_4H_{30}$: C,86.0;N,8.92;H,5.14).

Metal Complexes

Synthesis of aquo-N-methyltetra(p-sulfophenyl) porpthinato copper (II) trifluoromethane sulfonate.

Preparation of sodium aquo-N-methyltetra(sulfophenyl)porphinato copper (II) proceeds as follows: N-methyltetraphenylporphyrin is added to excess concentrated sulfuric acid with thorough mixing and heated on a steam bath for 2–4 days. After cooling, the solution is neutralized (either with $NaHCO_3$, $Na_2CO_3$, NaOH, $CaCO_3$) and the protonated salt of N-methyltetra(p-sulfophenyl)porphyrin is removed by several cycles of dissolution in methanol and precipitation with acetone. The copper complex is formed by a combination of copper trifluoromethanesulfonate with N-methylporphyrin in methanol. Gaseous ammonia is bubbled through the solution to remove the protons from the N-methylporphyrin. The trifluoromethane sulfonate salt is used because of its solubility and the anion is not presumed to have any therapeutic value.

Metals that readily complex with the porphyrins include copper, zinc, nickel, iron, cadmium, cobalt, palladium, silver, rhodium, and manganese. Metallo complexes and kinetic studies of porphyrins have appeared in the literature. (See references noted in the articles cited in the prior art statement).

Preferably, the metallo complexes are treated with solubilizing substituents and salt to facilitate their use as aqueous injections. For example, soluble solfonyl groups are readily added to the phenyl of the porphyrin. Adjuvant salts are well known in pharmaceutical and therapeutic compounding.

Anti-Tumor Activity

One of the compounds contemplated, namely, cuprate (3-), aqua [[4,4',4'',4'''-(21-methyl-21H,23H-porphine-5,10,15,20-tetraryl)tetrakis[benzenesulfonato]]=(5-)-$N^{21},N^{22},N^{23},N^{24}$]-,stereoisomer, sodium salt with trifluoromethanesulfon acid (1:4:1) was accepted for testing by the Drug Evaluation Branch of National Cancer Institute, under NSC No. 319418.

The indication of anti-tumor activity was determined based on the following procedure.

The model system employed is 6PS31. The schedule, summarized in Table I utilized 1 unit dose for 9 days. The tumor was PS-P-388, lymphocytic and the test animals were mice. Values of T/C, i.e., best response compared to its control, of 120 or greater are indicative that activity is present and that further testing is merited. Body weight change (T-C) of $\geq 4$ is also presumptive of activity.

The results indicate that the compound has activity against P388 tumors in animals (mice).

TABLE I

| Day Eval. | Tox | Total Inj. | Dose Unit/ Inj. (mg/kg body wt.) | T-C | T/C |
| --- | --- | --- | --- | --- | --- |
| 30 | 5 | 9 | 200 | −7.2 | |
| | | | 100 | −4.2 | 100 |
| | | | 50 | −3.3 | 92 |
| 30 | 5 | 9 | 50 | −2.6 | 119 |
| | | | 25 | −1.8 | 121 |
| | | | 12.50 | −1.1 | 112 |
| 30 | 5 | 9 | 50 | −2.8 | 101 |
| | | | 25 | −1.9 | 126 |
| | | | 12.50 | −0.4 | 126 |
| | | | 6.25 | −0.5 | 101 |

The term lymphocytic PSP-388 leukemia as noted in the claims and specification is equivalent to and means P388 leukemia.

What is claimed is:

1. The method of treating lymphocytic PS-P-388 leukemia in a mammal comprising the injection by injection of to said mammal of, sodium aquo-N-methyltetra(p-sulfophenyl)porphinato copper (II) trifluoromethane sulfonate in a daily dose rate of 6–100 mg/kilogram of body weight.

* * * * *

UNITED STATES PATENT OFFICE
CERTIFICATE OF CORRECTION

Patent No. 4,386,087                    Dated May 31, 1983

Inventor(s) David K. Lavallee

It is certified that error appears in the above-identified patent and that said Letters Patent are hereby corrected as shown below:

Claim 1, lines 2-3, delete "by injection of"

Signed and Sealed this

Thirteenth Day of September 1983

[SEAL]

Attest:

GERALD J. MOSSINGHOFF

Attesting Officer           Commissioner of Patents and Trademarks